United States Patent [19]

Beck et al.

[11] 3,949,024

[45] Apr. 6, 1976

[54] PHOSPHITE ESTERS OF HINDERED BIS AND TRIS PHENOLS

[75] Inventors: Walter Beck, Bedford; David Y. Kim, Lowell, both of Mass.

[73] Assignee: Stepan Chemical Company, Northfield, Ill.

[22] Filed: Dec. 1, 1971

[21] Appl. No.: 203,871

Related U.S. Application Data

[63] Continuation-in-part of Ser. No. 789,967, Jan. 8, 1969, abandoned.

[52] U.S. Cl. ........... 260/949; 260/45.7 PS; 260/814; 260/953
[51] Int. Cl.² ...................... C07F 9/145; C08K 5/53
[58] Field of Search ............................. 260/949, 953

[56] References Cited
UNITED STATES PATENTS

| | | | |
|---|---|---|---|
| 2,293,445 | 8/1942 | Nelson | 260/953 X |
| 3,112,286 | 11/1963 | Morris et al. | 260/953 X |

FOREIGN PATENTS OR APPLICATIONS

| | | | |
|---|---|---|---|
| 6,510,295 | 2/1967 | Netherlands | 260/953 |

*Primary Examiner*—Anton H. Sutto
*Attorney, Agent, or Firm*—Richard P. Crowley

[57] ABSTRACT

A phosphite ester of a hindered bis phenol of the formula:

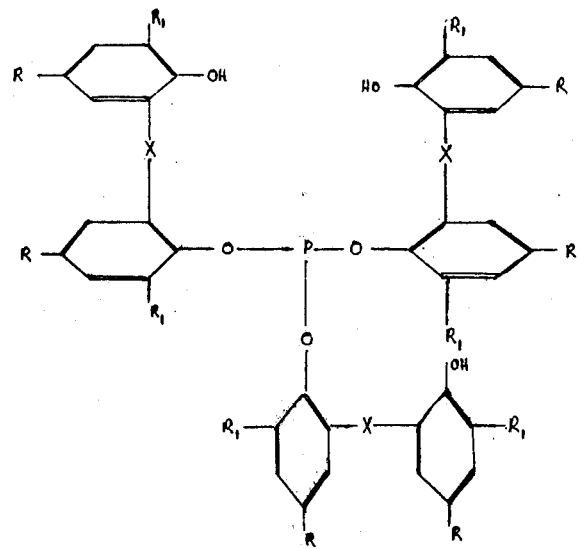

wherein X is an alkylene radical or sulfur, R is hydrogen or alkyl, and $R_1$ is alkyl, cycloalkyl or an alkyl-substituted aryl radical, which compounds are useful as stabilizers for polymeric materials.

17 Claims, No Drawings

PHOSPHITE ESTERS OF HINDERED BIS AND TRIS PHENOLS

REFERENCE TO PRIOR APPLICATION

This application is a continuation-in-part of application U.S. Ser. No. 789,967, filed Jan. 8, 1969, now abandoned.

BACKGROUND OF THE INVENTION

Phosphorus-containing compounds, such as phosphite compounds, are desirable for use as stabilizers for plastics and particularly for rubbers, especially for their metal chelating properties. Hindered phenols are also considered to be desirable as antioxidants, as evidenced by the wide use and acceptance of butylated hydroxy toluene. However, any efforts to form compounds which are combinations of hindered phenols and phosphite esters, to take advantage of the properties of both classes of compounds, have failed because the hindered phenol hydrogen is unreactive. This unreactivity of the hindered phenol is evidenced by the fact that reaction with sodium in liquid ammonia is necessary to replace the phenolic hydroxyl. U.S. Pat. No. 3,244,661 discloses triaryl phosphites, but these are not phosphite ester of hindered phenols. Thus, this relatively recent example of the state of the art supports the generally recognized theory that phosphite esters of hindered phenols are not obtainable.

It has now been found that phosphite esters of hindered phenols, particularly bis phenols, can be prepared and are particularly valuable as stabilizers for plastics and rubbers.

SUMMARY OF THE INVENTION

This invention relates to compounds which are phosphite esters of hindered bis phenols, their method of preparation, and their use as stablizers and antioxidants in polymers.

The novel compounds of the present invention are represented by the formula:

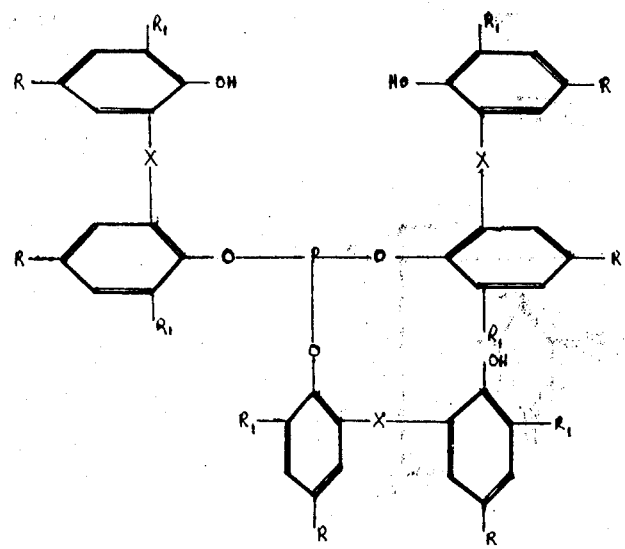

(I)

wherein X is sulfur or lower alkylene; e.g., a 1–4 carbon alkylene radical, preferably methylene; R is hydrogen or an alkyl radical; e.g., a $C_1$–$C_{12}$ radical; and $R_1$ is an alkyl radical; e.g., $C_1$–$C_{12}$, preferably where the carbon adjacent to the ring is branched; e.g., a $C_3$–$C_{12}$ radical, and more preferably, a tertiary radical, a cycloalkyl radical, or an X-linked alkylaryl radical, such as an alkyl-substituted phenolic radical having the formula:

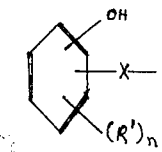

(II)

where $n$ is 1, 2, 3 or 4, preferably 1 or 2, and R' is an alkyl or cycloalkyl radical; e.g., an alkyl radical of R or $R_1$, and preferably, where $n$ is 2, R' is $R_1$ and is ortho to the hydroxyl group, where R' is R and is para to the hydroxyl group. The hydroxyl group may be ortho or para to the X-linked radical, preferably ortho. Where $n$ is 1, the R' may be $R_1$, or R, and preferably $R_1$, ortho or para to the hydroxyl group. In all the formulas, each R, R' and $R_1$ may be the same or different.

Preferably then, $R_1$ may be:

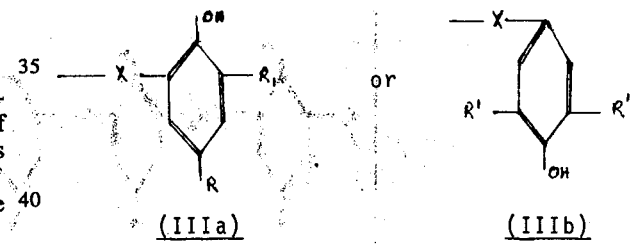

(IIIa) or (IIIb)

Phosphite esters of the hindered bis phenols may have structures of a hindered bis phenol or a hindered alkyl-phenolic bis phenol, or a mixture thereof where only one or more of the hindered bis phenol groups have one or two alkyl-phenolic substituents.
Some preferred compounds would be represented by the formulas as follows:
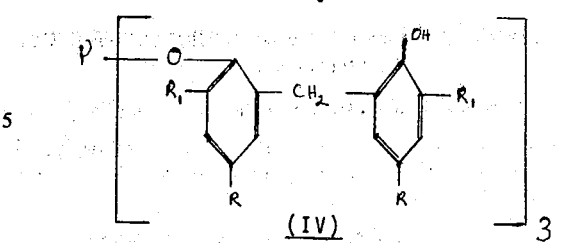
(IV)
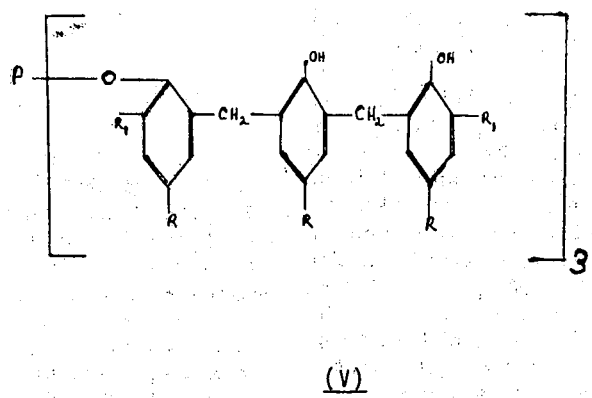
(V)
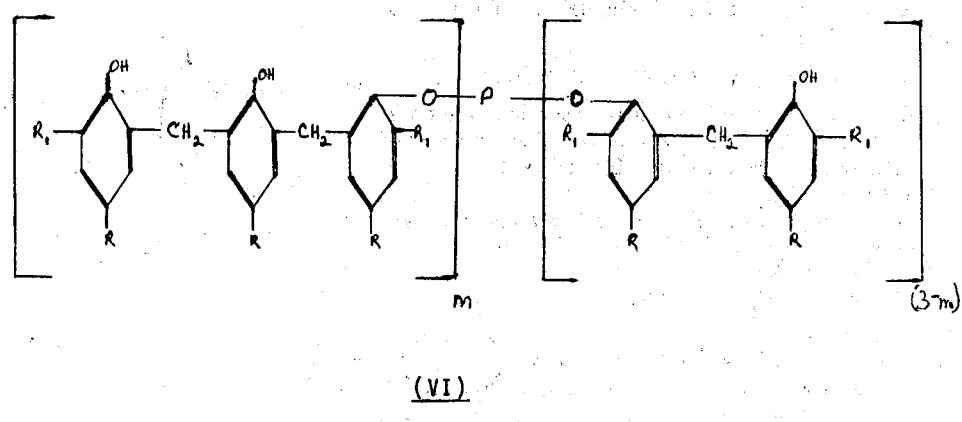
(VI)
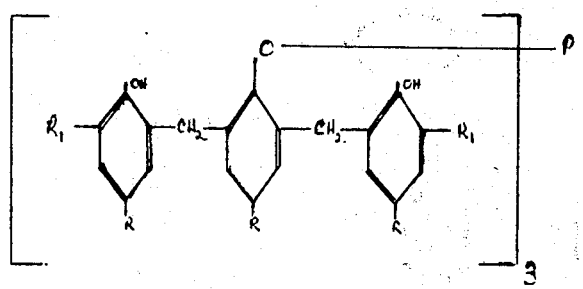
(VII)

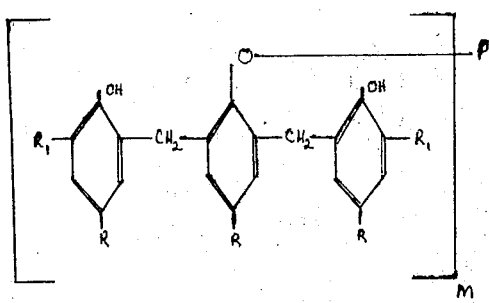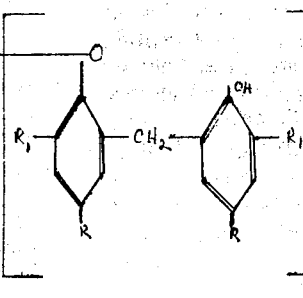

(VIII)

where $R_1$ is a tertiary butyl radical, and R is a $C_1$–$C_{12}$ radical, such as methyl, ethyl, tertiary butyl, hexyl, cyclohexyl, octyl, nonyl, etc., and where m is 1, 2 or 3.

The above formulas are illustrative of representative formulas of the invention, it being recognized that the methylene radicals may be X as previously defined and that the phosphorus-oxygen linkage may be to either end phenolic group or to the central phenolic group, or a mixture thereof, but not to three phenolic groups of the same alkylaryl-substituted tris phenol.

The compounds of the present invention are prepared by reacting a substituted phenol; e.g., an ortho-substituted phenol, preferably a p-alkyl ortho-substituted phenol; e.g., $R_1$-substituted phenol, with an aldehyde or with a sulfur halide. The thus formed hindered bis phenol is then reacted, preferably under anhydrous conditions, with a trivalent phosphorus compound, preferably a phosphorus trihalide, such as phosphorus trichloride or phosphorus tribromide, or in a transesterification reaction, in bulk or in a solvent; e.g., a hydrocarbon, such as toluene.

DETAILED DESCRIPTION

The phosphite esters of the hindered bis phenols range from viscous liquids to solids depending upon the particular reactants and the nature of the reaction conditions.

The phenol employed in preparing the compounds of the present invention may be a hindered alkyl-substituted phenol (hindered), a hindered alkylene bis alkyl phenol or a hindered thiobis alkyl phenol. The aldehyde is preferably formaldehyde or paraformaldehyde, and the sulfur halide is preferably sulfur dichloride. The ratio of aldehyde or sulfur halide to phenol may range from 0.5–0.75 to 1, preferably 0.5–0.66 to 1, more preferably two moles of phenol are used per mole of aldehyde or sulfur halide. Where a hindered bis phenol is employed, of course, the step of reacting the phenol and the aldehyde is not employed. The reaction is catalyzed and is preferably carried out in a solvent system, more particularly, toluene. In order to avoid any hydrolysis of the product, any water present is removed, as by distillation, so that the reaction of the bis phenol and trivalent phosphorus compound is carried out under anhydrous or substantially anhydrous conditions. If the phosphorus compound employed is phosphorus trichloride, refluxing and sparging with an inert gas, such as nitrogen, or other suitable means are employed to remove any hydrogen chloride present. Preferred phenols include 6-t-butyl p-cresol, 6-t-butyl p-nonyl phenol, 6-nonyl p-cresol and 2,4 di-nonyl phenol.

The reaction of the bis phenol with the trivalent phosphorus compound may be carried out in bulk or in a suitable organic solvent, such as a hydrocarbon such as benzene, toluene, xylene, or mixtures thereof. The temperatures employed generally range from 40°C to 80°C, but the specific temperatures are selected with regard to the specific reactants employed. The ratio of trivalent phosphorus compound to bis phenol may range from 0.05–0.33 to 1. Preferably 3 moles of bis phenol are employed per mole of phosphorus compound. Although a phosphorus halide, like the trichloride, are preferably employed, other trivalent phosphorus compounds known to the art may be employed in the esterification or transesterification reaction.

Typical bis phenols which may be employed alone or in combination include, but are not limited to: 2.2'λ methylene bis (6-t-butyl p-cresol); 2,2'methylene bis (6-nonyl p-cresol); 2,2'methylene bis (6-octyl p-cresol); 2,2'methylene bis (6-t-butyl p-nonyl phenol); 2,6, di-tertiary butyl 4 (2-OH-3-nonyl-5-methyl benzyl) phenol; 2,6, di-t-butyl 4 (2-OH-3,5-nonyl benzyl) phenol; 2,2'-methylene bis (6 cyclopentene p-cresol); 2,2'-methylene bis (6 cyclopentene, p-nonyl phenol); 2,6 (2-OH-3-t butyl-5-methyl benzyl) p-cresol and their thio analogues; e.g., 2,2'thio bis (6-t-butyl p-cresol).

The phosphite esters of the invention include, but are not limited to: tris (methylene bis-2-(4 methyl-6-t-butyl phenol)-2'(4 methyl-6-t-butyl phenyl)) phosphite; tris(methylene bis-2-(4-nonyl-6-t-butyl phenol)-2'-(4-nonyl)-6-t-butyl phenyl)) phosphite; tris (thio bis-2-(6-t-butyl p-cresol)-2'-(6-t-butyl p-cresol)) phosphite; tris (methylene bis-2-(3,5 di-nonyl phenol) 2'-(4-nonyl-6 (3,5-di-nonyl-6-OH-benzyl) phenyl)) phosphite; and tris (methylene bis-2-(6 dicyclopentene p-cresol) 2' (6 dicyclopentene p-cresyl)) phosphite.

The compounds have utility as stabilizers and antioxidants for plastic resins and elastomers. They are particularly useful in hydrocarbon resins and conjugate diene elastomers subject to degradation such as polyolefins, such as $C_2$–$C_4$ olefinic resins; e.g., polyethylene, polypropylene, ethylene-propylene copolymers, ethylenepropylene-diene copolymers and copolymers of styrene and butadiene; e.g., styrene-butadiene rubber (SBR).

The phosphite esters of hindered bis phenols are useful in preventing a change in color or mechanical strength properties during processing or storage of the particular material with which it is employed. The phosphite esters may be used alone or in combination with and as a component of other stabilizer systems and may be used in materials such as vinyl resins, such as polyvinyl chloride and vinyl chloride - vinyl acetate copolymers, polyesters; e.g., iso and terephthalactic acid glycol polyester resins, urethanes, acrylic resins; styrene resins, such as polystyrene and rubber-modified polystyrene, and in other polymers and resins which normally develop color on storage or during processing at elevated temperatures.

The compounds of the present invention are also suitable for use with natural and synthetic elastomers such as rubbery styrene-butadiene copolymers (SBR), acrylonitrile-butadiene copolymer (ABS), polybutadiene, butyl rubber, acrylonitrile-styrene copolymers, natural rubber, carboxylated elastomers, and ethylene-propylene rubbery copolymers. The compounds of the present invention are also particularly suitable for use in olefin resins such as polyethylene, polypropylene and propylene copolymers.

The compounds of the present invention may be added directly to the polymer by melting or dispersing onto the material to be stabilized or added to solutions or emulsions of the polymers. The compounds of the present invention are preferably employed at a level of about 0.1 to 5% by weight, preferably 0.5 to 2.0% by weight based on the weight of the material to be protected The following nonlimiting examples illustrate the preparation of the novel compounds of the present invention:

EXAMPLE I 325 g of mono t-butyl p-cresol (2 moles) were dissolved in 200 g toluene to which was added 30 g of paraformaldehyde (1 mole) and 5 g of concentrated hydrochloric acid. The mixture was heated to 75°C for one hour, then refluxed under a Dean Stark trap until water distillation ceased. The reaction mixture was cooled to 60°C, and 45.6 g of phosphorus trichloride (0.33 moles) was added over a period of one-half hour. The mixture was stirred at 60°C for one-half hour, then heated to reflux, and refluxed for seven hours, to drive off hydrogen chloride. Nitrogen sparging, to assist in gas removal, was instituted when the gas evolution slowed down.

The reaction mixture is then cooled, and the white solid that separates is recrystallized from toluene and dried at 100°C. The melting point of the product, tris (methylene-bis-2-(6-t-butyl p-cresol) 2'-(6-t-butyl p-cresyl)) phosphite, was 126°C.

| Calculated for $C_{69}H_{93}O_6P$ | |
|---|---|
| Phosphorus | 2.95% |
| Carbon | 78.50% |
| Hydrogen | 8.95% |
| Found | |
| Phosphorus | 2.69% |
| Carbon | 77.40% |
| Hydrogen | 8.49% |

EXAMPLE II 550 g of mono t-butyl p-nonyl phenol (2 moles) was dissolved in 250 cc of toluene to which was added 30 g of paraformaldehyde (1 mole) and 5 grams of oxalic acid. The mixture was refluxed under a Dean stark water trap until substantially all water is removed.

The mixture was cooled to 65°C and 45.6 g of phosphorus trichloride (⅓ mole) was added over one-half hour. The mixture was held at 60°–65°C for one-half hour, then heated to reflux and refluxed seven hours. At the end of this time, nitrogen was sparged through the mixture to remove dissolved hydrogen chloride. The toluene was distilled off. The residue, tris (methylene-bis-2-(6-t-butyl p-nonyl phenyl)-2'-(6-t-butyl p-nonyl phenol)) phosphite, was an amber viscous liquid.

EXAMPLE III 328 g t-butyl p-crescol was dissolved in toluene. 67.5 g of sulfur monochloride (1 mole) was added dropwise over one-half hour and the mixture was heated to reflux for one hour.

The mixture was cooled to 60°–65°C, and 45.6 g of phosphorus trichloride (⅓ mole) was added over a period of one-half hour. The mixture was refluxed seven hours, and then sparged with nitrogen to remove hydrogen chloride. The mixture was cooled, and the solid, tris (this-bis-2- (6-t-butyl p-nonyl phenol)-2'-(6-t-butyl p-nonyl phenyl)) phosphite, which separated, was recrystallized from toluene.

EXAMPLE IV 930 g (1 mole) of 2,6 di-methylene para nonyl phenol bis 2,2' (4,6 di-nonyl phenol), prepared by the reaction of 1 molar quantity of nonyl phenol and twice molar quantities of paraformaldehyde, using an alkaline catalyst with di-nonyl phenol, is dissolved in 500 ml of toluene.

The solution is heated to 60°–65°C, and 45.6 g (0.33 mole) of PCl₃ is added slowly over a half-hour period. The mixture is refluxed for seven hours using a nitrogen sparge to facilitate removal of hydrogen chloride. The toluene is removed by distillation under reduced pressure leaving the product, tris (methylene bis-2-(4,6-di-nonyl phenol)-2'-(4 nonyl-6-(2 OH-3,5-di-nonyl benzyl) phenyl)) phosphite as a viscous dark amber liquid.

As stated above, that the compounds of the present invention could be prepared is entirely unexpected because of the nonreactivity of the hindered phenol hydroxyl, and in addition, because of the bulky molecules involved, it is also unexpected that the herein described reaction would occur because of steric hindrance.

The phosphite esters of the present invention are employed as stabilizers and antioxidants alone or in combination with other additives in gasoline, waxes, greases, natural and synthetic lubricating oils, jet fuel, heating fuel oil, and as a general petroleum product additive as a stabilizer, or for its phosphorus content.

What we claim is:
1. A phosphite ester of a hindered bis phenol represented by the formula:

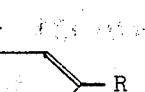

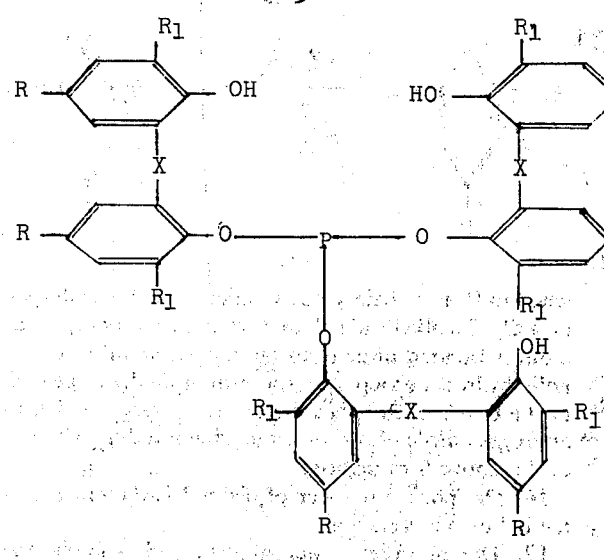

wherein X is sulfur, $R_1$ is a $C_4$–$C_{12}$ alkyl radical wherein the carbon adjacent to the ring is branched, and R is selected from the group consisting of hydrogen and a $C_1$–$C_{12}$ alkyl radical.

2. The phosphite ester of claim 1 wherein $R_1$ is a tertiary butyl radical.

3. The phosphite ester of claim 1 wherein R is a nonyl or methyl radical.

4. The phosphite ester of claim 1 wherein R is selected from the group consisting of methyl and nonyl radicals and $R_1$ is a tertiary butyl radical.

5. The phosphite ester of claim 1 which is tris (thio bis 2-(4 methyl 6-t-butyl phenol)-2'-(4 methyl 6-butyl phenyl)) phosphite.

6. The phosphite ester of claim 1 which is tris (thio bis-2-(4-nonyl-6-t-butyl phenol)-2'-(-4-nonyl-6-t-butyl phenyl)) phosphite.

7. The phosphite ester of claim 1 which is tris (thio-bis-2-(6-t-butyl p-cresol)-2'-(6-t-butyl p-cresyl)) phosphite.

8. A phosphite ester represented by the formula:

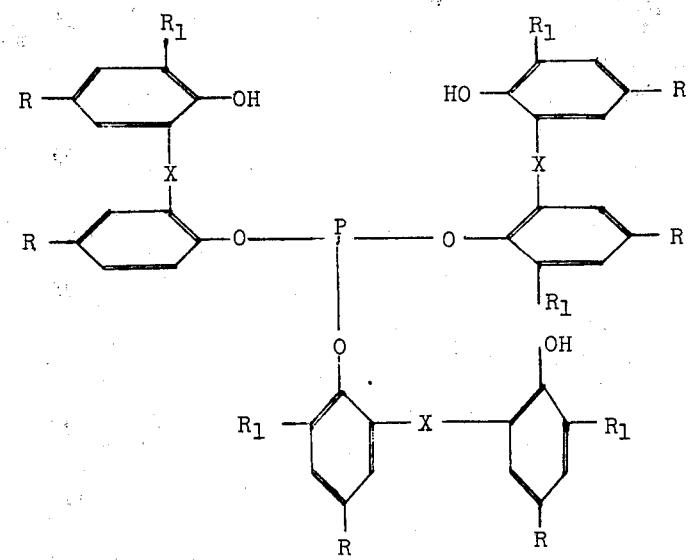

wherein X is sulfur, $R_1$ is a $C_1$–$C_{12}$ alkyl radical, a cycloalkyl radical or an alkyl-substituted phenol radical represented by the formula:

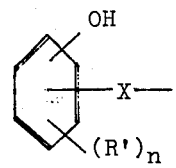

where R' is an radical, radica, and n is 1, 2, 3 or 4, and R is selected from the group consisting of hydrogen and a $C_1$–$C_{12}$ alkyl radical.

9. The phosphite ester of claim 8 wherein the alkyl-substituted phenolic radical is represented by the formula:

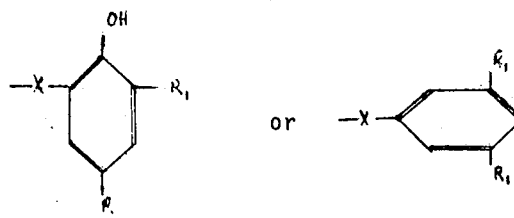

or

10. The phosphite ester of claim 8 wherein $R_1$ is a $C_4$–$C_{12}$ alkyl radical wherein the carbon adjacent the ring is branched.

11. The phosphite ester of claim 8 wherein R is a $C_8$–$C_9$ alkyl radical.

12. The phosphite ester of claim 8 wherein $R_1$ and R are tertiary butyl radicals.

13. The phosphite ester of claim 8 wherein, $R_1$ is a tertiary butyl radical and R is a $C_1$–$C_{12}$ alkyl radical.

14. The phosphite ester of claim 9 wherein only one phenolic radical is linked to the phenol ring having the unreacted hydroxyl group.

15. A phosphite ester of a hindered tris phenol, the hindered tris phenol represented by the structural formula:

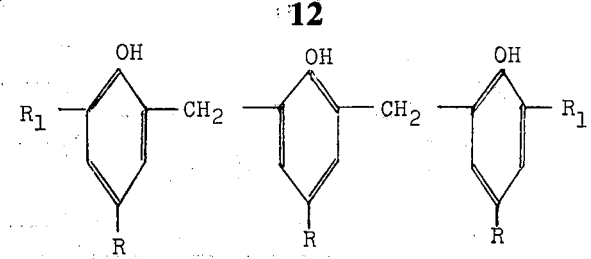

wherein $R_1$ is a tertiary butyl radical and R is hydrogen or a $C_1$–$C_{12}$ alkyl radical, and wherein the phosphorus atom is bonded directly to an oxygen atom of a phenolic hydroxyl group after removal of the hydrogen, all of the bonds of the phosphorus atom being bonded to an oxygen atom of two or three a hindered tris phenols of the above formulation.

16. The phosphite ester of claim 15 wherein R is a methyl or nonyl radical.

17. The phosphite ester of claim 15 wherein the phosphorus atom is bonded to the hydroxyl oxygen atom of three hindered tris phenols.

* * * * *